(12) United States Patent
Ohinata et al.

(10) Patent No.: US 8,946,164 B2
(45) Date of Patent: Feb. 3, 2015

(54) BIOACTIVE PEPTIDE

(75) Inventors: Kousaku Ohinata, Kyoto (JP); Ayako Oda, Uji (JP)

(73) Assignee: Kyoto University (JP)

( * ) Notice: Subject to any disclaimer, the term of this patent is extended or adjusted under 35 U.S.C. 154(b) by 0 days.

(21) Appl. No.: 13/640,002

(22) PCT Filed: Apr. 6, 2011

(86) PCT No.: PCT/JP2011/058728
§ 371 (c)(1),
(2), (4) Date: Nov. 29, 2012

(87) PCT Pub. No.: WO2011/126054
PCT Pub. Date: Oct. 13, 2011

(65) Prior Publication Data
US 2013/0203677 A1 Aug. 8, 2013

(30) Foreign Application Priority Data

Apr. 7, 2010 (JP) ................................. 2010-088531

(51) Int. Cl.
| | | |
|---|---|---|
| *A61K 31/00* | (2006.01) | |
| *A61K 38/00* | (2006.01) | |
| *A61K 38/04* | (2006.01) | |
| *C07K 5/107* | (2006.01) | |
| *A23L 1/305* | (2006.01) | |
| *C07K 5/083* | (2006.01) | |
| *C07K 7/06* | (2006.01) | |
| *C07K 14/465* | (2006.01) | |
| *C07K 14/77* | (2006.01) | |

(52) U.S. Cl.
CPC .............. *C07K 5/1016* (2013.01); *A23L 1/3053* (2013.01); *A61K 38/04* (2013.01); *C07K 5/0808* (2013.01); *C07K 7/06* (2013.01); *C07K 14/465* (2013.01); *C07K 14/77* (2013.01)
USPC ....... 514/17.6; 514/17.5; 514/21.8; 514/21.9; 530/300; 530/330

(58) Field of Classification Search
None
See application file for complete search history.

(56) References Cited

U.S. PATENT DOCUMENTS 6,451,578 B1 * 9/2002 Simons et al. ............. 435/235.1

FOREIGN PATENT DOCUMENTS

| FR | WO2006042661 A2 * | 4/2006 | ............. C07K 14/47 |
|---|---|---|---|
| JP | H11-285362 A | 10/1999 | |
| JP | 2005-121380 A | 5/2005 | |

OTHER PUBLICATIONS

Ohinata, K. "Functional Peptide derived from chicken egg protein—particularly about mental stress relief effect—" The 57th Proceedings of Japanese Society of Food Science and Technology; Sep. 1, 2010, p. 174.
Tokarski, C. et al. "Identification of proteins in renaissance paintings by proteomics"; Anal. Chem., vol. 78, No. 5, Mar. 1, 2006; 1494-1502.
Wu, J.T., et al. "Protein digest analysis by pressurized capillary electrochromatography using an ion trap storage/reflectron time-of-flight mass detector"; Anal. Chem. 1997, 69, 2008-2913.
Suzuki, C., et al. "[Trp$^5$]-oryzatensin (5-9), an Agonist Peptide for Complement C3a Receptor, Exhibits Anxiolytic-Like Effect Mediated by Prostaglandin $E_2$"; Peptide Science 2009, 2010, pp. 269-272.
International Search Report prepared by the Japanese Patent Office on Jun. 21, 2011, for International Application No. PCT/JP2011/058728.
Kanegawa et al., "Dipeptide Tyr-Leu (YL) exhibits anxiolytic-like activity after oral administration via activating serotonin 5-HT$_{1A}$, dopamine $D_1$ and GABA$_a$ receptors in mice," FEBS Letters, 2010, vol. 584, No. 3, pp. 599-604.
Extended European Search Report dated Jan. 10, 2014 for corresponding EP Patent Application No. 11765954.0, 6 pages.

* cited by examiner

*Primary Examiner* — Olga N Chernyshev
(74) *Attorney, Agent, or Firm* — Sheridan Ross P.C.

(57) ABSTRACT

The present invention provides a pharmaceutical or a food that comprises, as an active ingredient, at least one peptide selected from the group consisting of Val-Tyr-Leu-Pro-Arg (SEQ ID NO:1), Tyr-Leu-Pro-Arg (SEQ ID NO:2), and Leu-Pro-Arg (SEQ ID NO:3), or an analog thereof.

4 Claims, 11 Drawing Sheets

Fig. 10
A. DP$_1$ antagonist
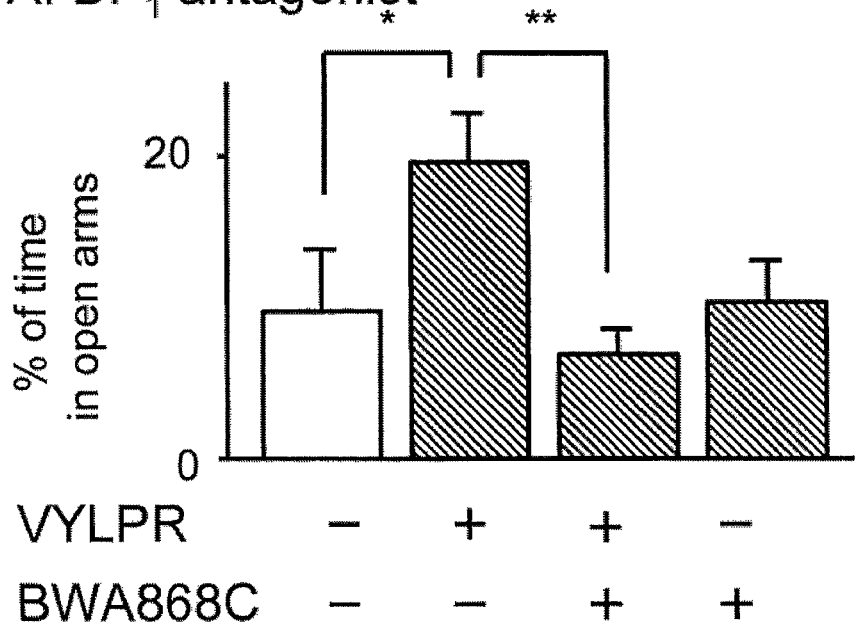
B. adenosine A$_{2A}$ antagonist
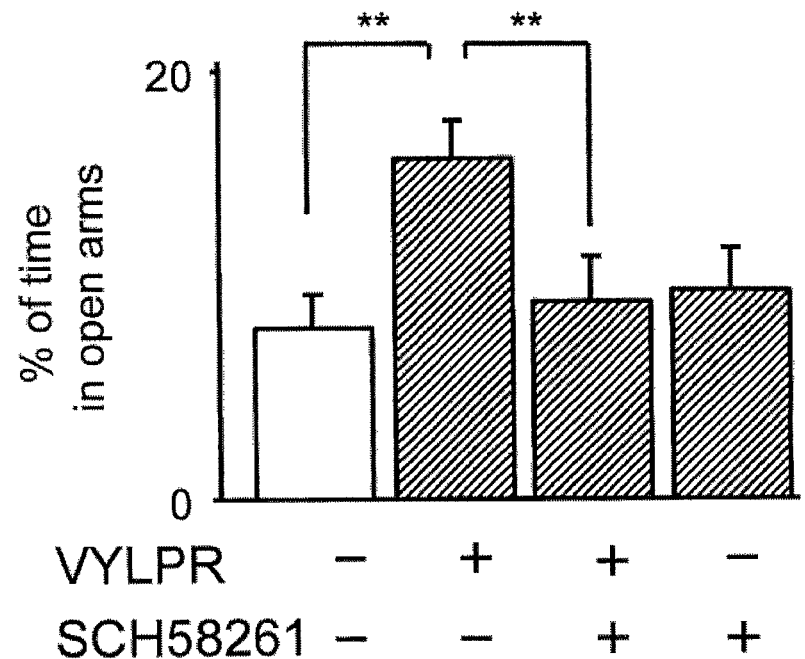

ably found that short-chain peptides each including "Leu-Pro-Arg" (SEQ ID NO:3) as a common sequence, such as Val-Tyr-Leu-Pro-Arg (SEQ ID NO:1), Tyr-Leu-Pro-Arg (SEQ ID NO:2), and Leu-Pro-Arg (SEQ ID NO:3), have potent anxiolytic, sedative, and like effects, and have the effect of activating prostaglandins and $GABA_A$ receptors, thereby accomplishing the invention.

The present invention provides peptides, pharmaceuticals, anxiolytic or a sleep-enhancing food, and a method for relieving anxiety or enhancing sleep, as given below.

Item 1. At least one peptide selected from the group consisting of Val-Tyr-Leu-Pro-Arg (SEQ ID NO:1), Tyr-Leu-Pro-Arg (SEQ ID NO:2), and Leu-Pro-Arg (SEQ ID NO:3), or an analog thereof.

Item 2: A pharmaceutical or a pharmaceutical composition comprising the peptide or analog thereof according to Item 1.

Item 3: The pharmaceutical or the pharmaceutical composition according to Item 1 or 2, which is an anxiolytic drug, a sleep-inducing drug, a sleep-enhancing drug, a drug for treating schizophrenia, or an antidepressant drug.

Item 4: An anxiolytic or sleep-enhancing food comprising the peptide or analog thereof according to Item 1.

Item 5: A method for relieving anxiety or enhancing sleep, comprising administering an effective amount of the peptide according to Item 1 to a subject in need thereof.

Advantageous Effects of Invention

The anxiolytic drugs, drugs for treating sleep disorders, drugs for treating schizophrenia, antidepressant drugs, and drugs for preventing these diseases that contain as active ingredients the peptides of the invention or analogs thereof have few side effects and are suitable for long-term use.

Furthermore, the drugs of the invention are effective by oral administration.

Furthermore, natural short-chain peptides can be ingested as food; therefore, when ingested as food by individuals who are not ill but who have anxious tendencies or trouble sleeping, such peptides can be expected to prevent diseases in such individuals.

The peptides of the invention and analogs thereof have the effect of activating prostaglandins and $GABA_A$ receptors, and are thus expected to have the effect of preventing or treating various diseases attributed to the effect of activating these receptors.

Furthermore, the peptides of the invention and analogs thereof are free of side effects caused by the activation of opioid receptor agonists.

BIOACTIVE PEPTIDE

CROSS REFERENCE TO RELATED APPLICATIONS

This application is a national stage application under 35 U.S.C. 371 of PCT Application No. PCT/JP2011/058728 having an international filing date of 6 Apr. 2011, which designated the United States, which PCT application claimed the benefit of Japanese Application No. 2010-088531 2010 filed 7 Apr. 2010, the entire disclosure of which is incorporated herein by reference.

TECHNICAL FIELD

The present invention provides a peptide having a neuromodulatory effect, and a pharmaceutical or a food comprising the peptide.

REFERENCE TO SEQUENCE LISTING

This application contains a Sequence Listing submitted as an electronic text file entitled "20128H Sequence Listing" having a size in bytes of 1 kb, and created Oct. 1, 2012. The information contained in this electronic file is hereby incorporated by reference in its entirety pursuant to 37 CFR §1.52 (e) (5).

BACKGROUND ART

Reflecting today's stressful society, an increasing number of individuals with psychiatric disorders such as anxiety disorders, schizophrenia, and depression has been a problem. Anxiety is inherently necessary as a warning to help living organisms avoid danger. However, it is known that excessive anxiety involves the onset or the progression of symptoms of psychiatric disorders as mentioned above, and also increases the risk of the onset of lifestyle-related diseases. Therefore, the development of foods and pharmaceuticals for relieving mental stress has been desired. Preferably, compounds having such anxiolytic effects can be manufactured at low costs and are effective by oral administration.

Ovalbumin is a main egg-white protein and is contained in various foods.

Patent Literature 1 discloses that soymorphin derived from β-conglycinin, which is a major soy protein, has anxiolytic effects.

CITATION LIST

Patent Literature

Patent Literature 1: Japanese Unexamined Patent Publication No. H11-285362

SUMMARY OF THE INVENTION

Problem to be Solved by the Invention

An object of the present invention is to provide a pharmaceutical and a food having anxiolytic, sedative, sleep-enhancing, and like effects, and having few or no side effects.

Means to Solve the Problem

Figure 7:
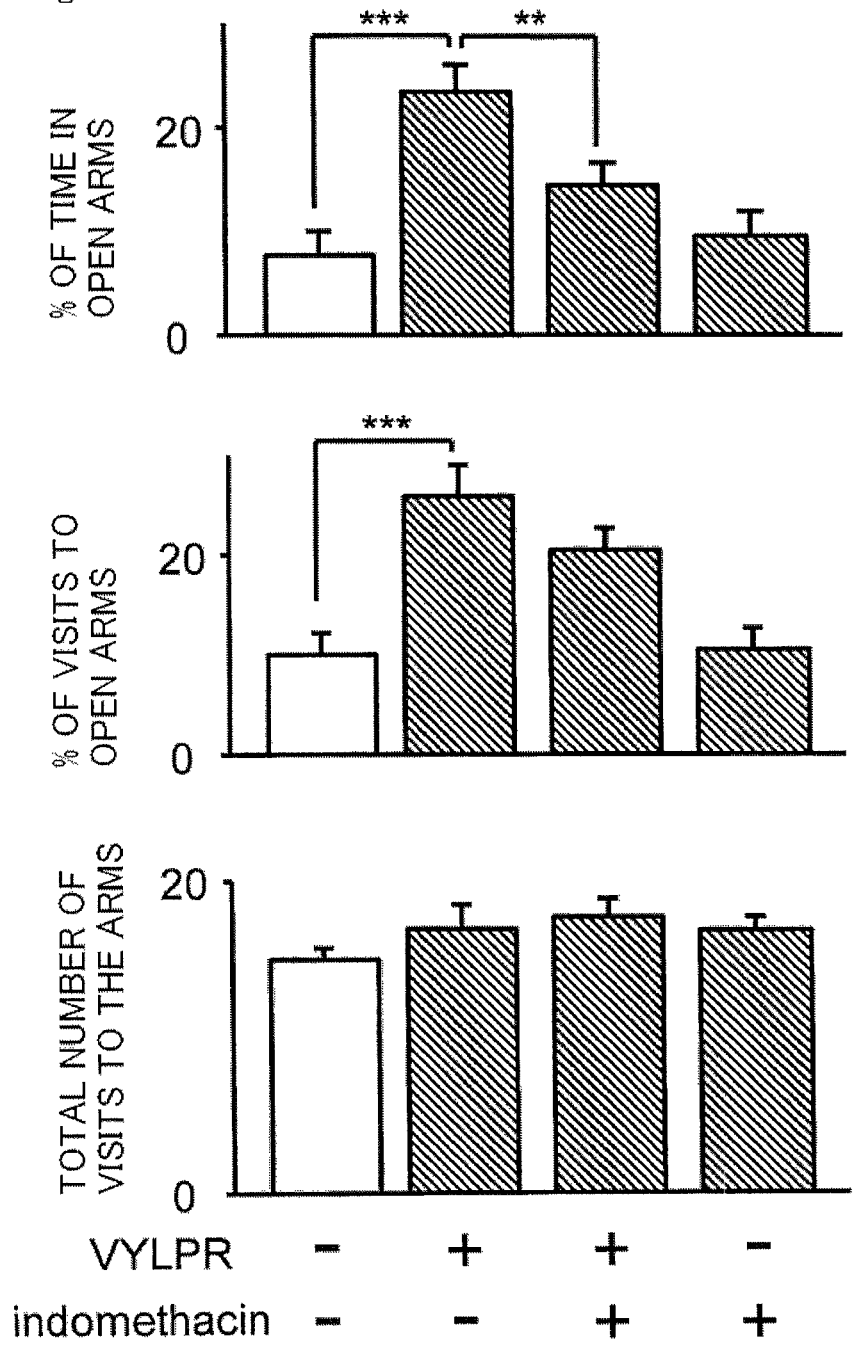

In order to achieve the above object, the inventors investigated various peptides for anxiolytic effects, and conse- FIG. 7 shows the effect of a COX inhibitor on the VYLPR (SEQ ID NO:1) anxiolytic effect, mean±SEM (n=12 to 15, p<0.01, *p<0.001.

Figure 8:
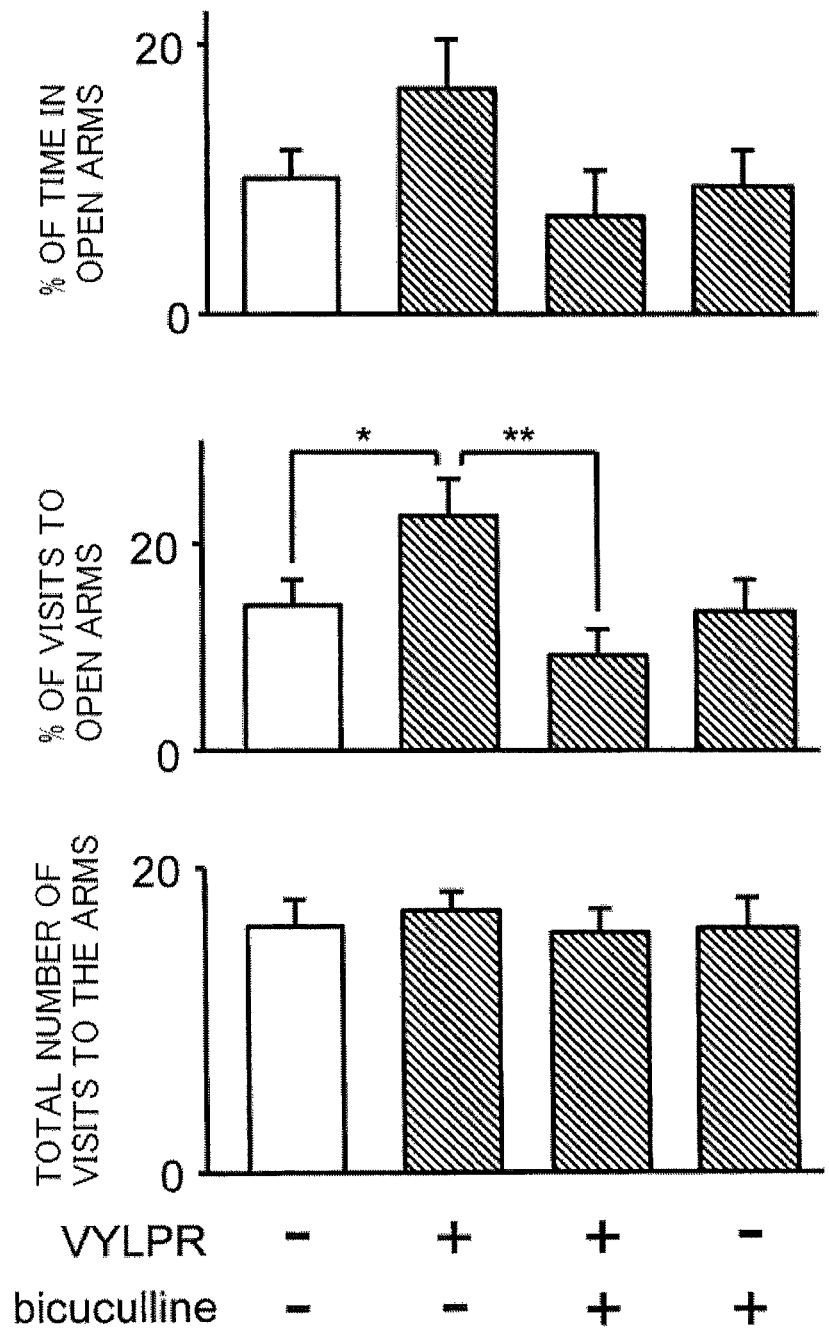

FIG. 8 shows the effect of a $GABA_A$ receptor antagonist on the VYLPR (SEQ ID NO:1) anxiolytic effect, mean±SEM (n=9 to 12, *p<0.05, **p<0.01.

Figure 9:
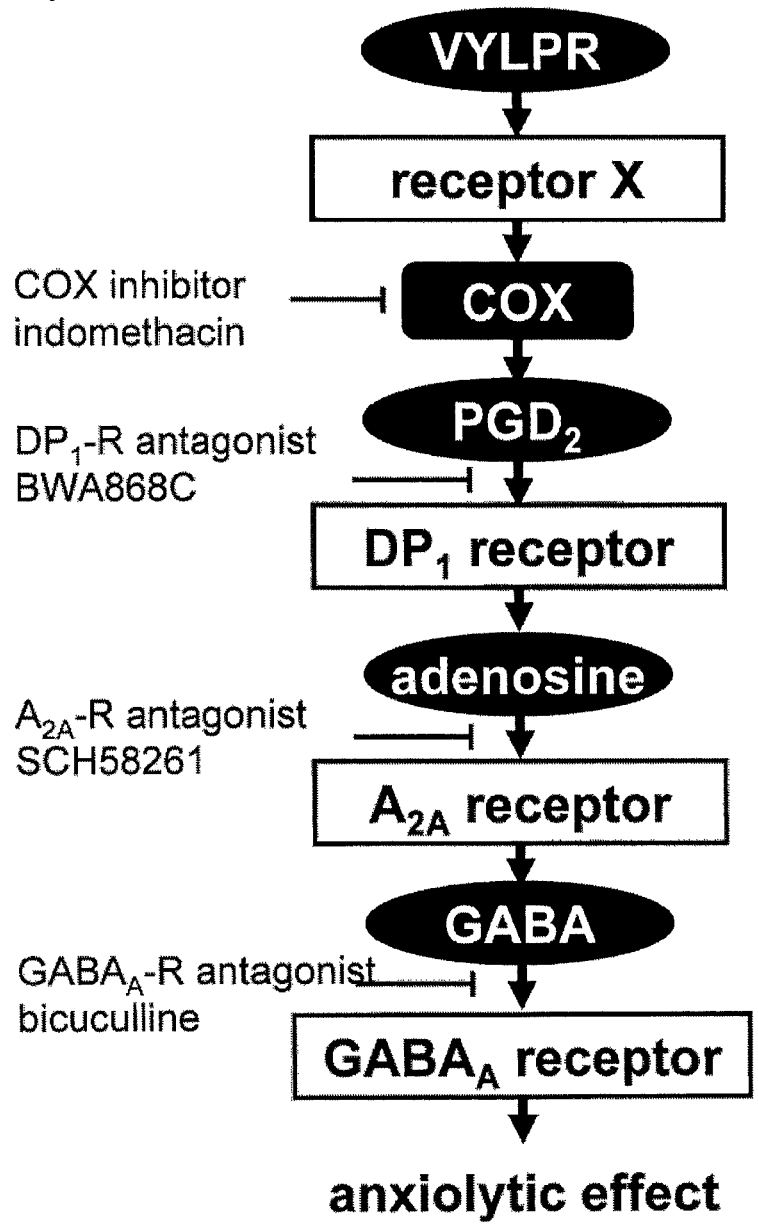

FIG. 9 shows a presumed anxiolytic mechanism of VYLPR (SEQ ID NO:1).

FIG. 10 shows the effects of (A) a prostaglandin DP1 receptor antagonist and (B) an adenosine A2A receptor antagonist on the VYLPR (SEQ ID NO:1) anxiolytic effect, (A: n=7 to 9; B: n=9-23). The VYLPR (SEQ ID NO:1) anxiolytic effect was inhibited by the antagonists for a DP1 receptor and A2A receptor. Thus, it was found that VYLPR (SEQ ID NO:1) anxiolytic effect occurred as a result of promoted release of PGD2 and adenosine.

Figure 11:
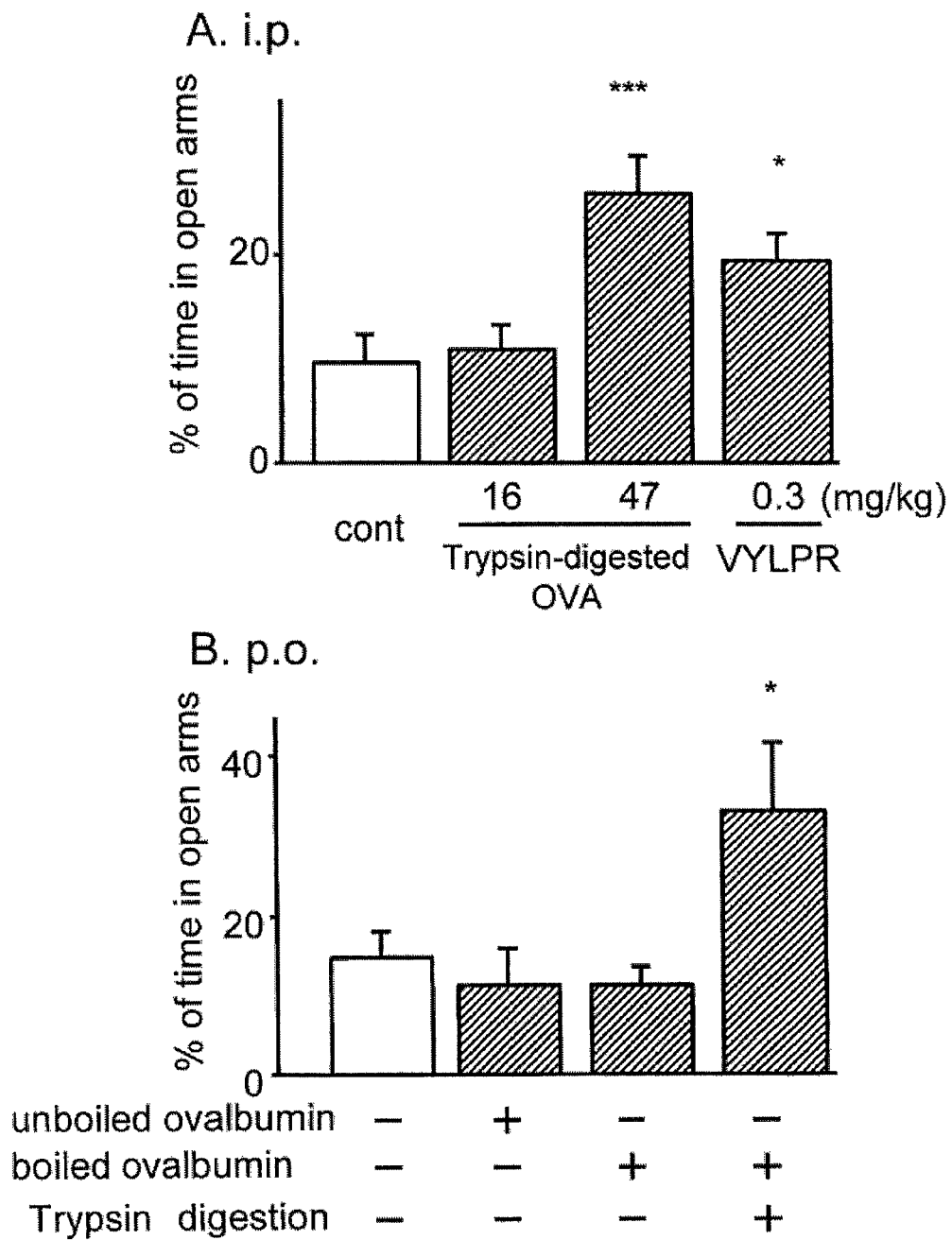

FIG. 11 shows the anxiolytic effects of trypsin-digested ovalbumin (OVA), (A) an anxiolytic effect by intraperitoneal administration of trypsin-digested OVA, and (B) an anxiolytic effect by oral administration. Undigested ovalbumin did not show anxiolytic effects (A: n=8 to 10; B: n=6 to 7).

EMBODIMENTS FOR CARRYING OUT THE INVENTION

Pharmacological Effects

Figure 1:
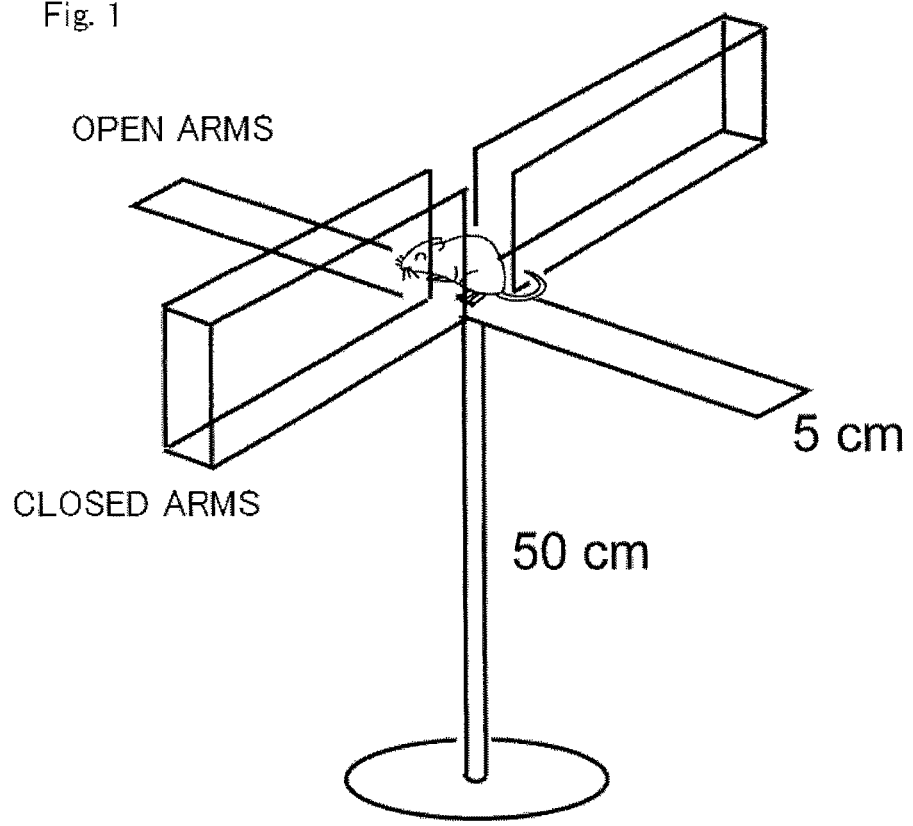
FIG. 1 shows an elevated plus-maze.
Figure 2:
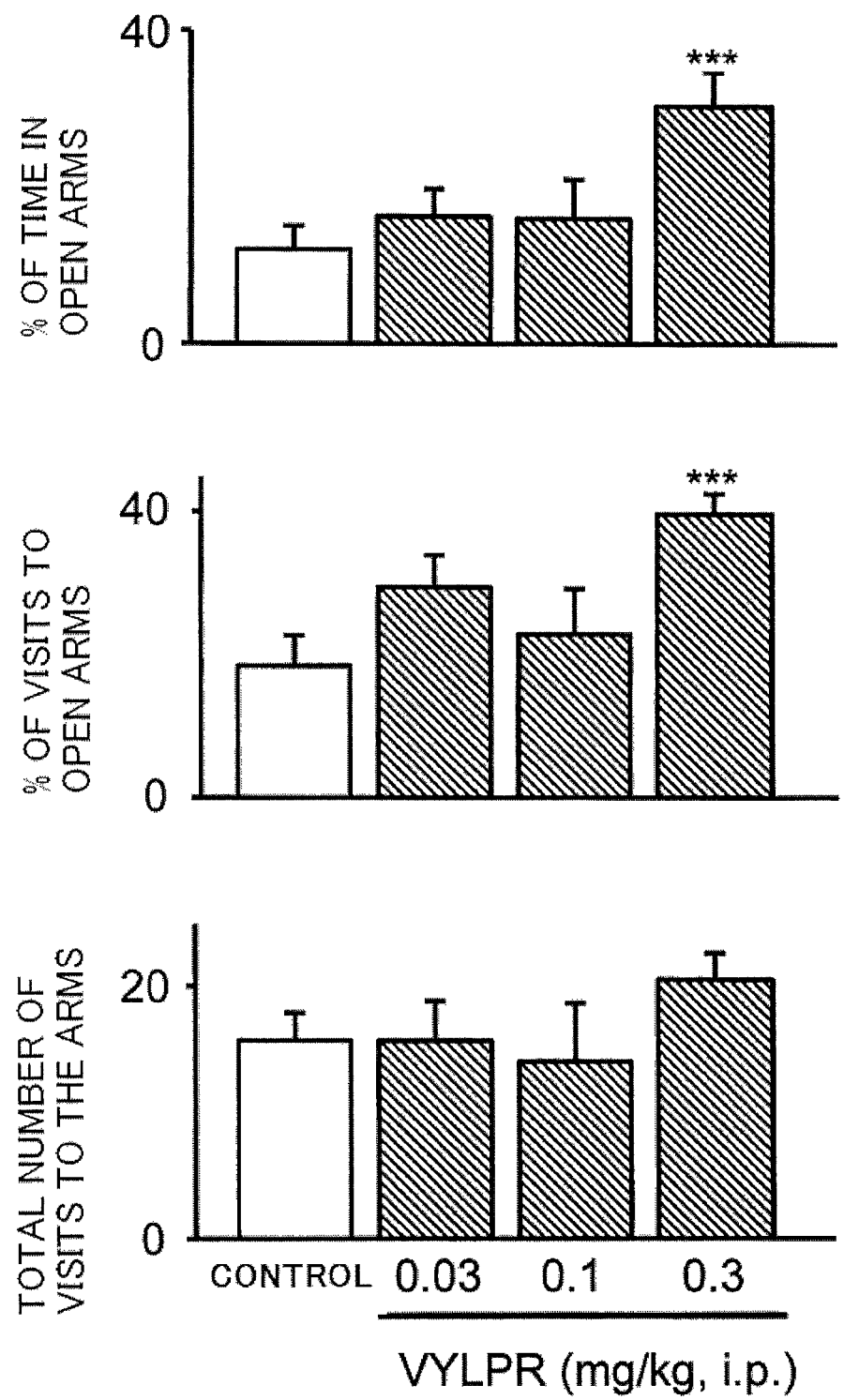
FIG. 2 shows the anxiolytic effect of intraperitoneally administered VYLPR (SEQ ID NO:1) (Example 1), mean±SEM (n=5 to 10), ***$p<0.001$ vs. control.
Figure 3:
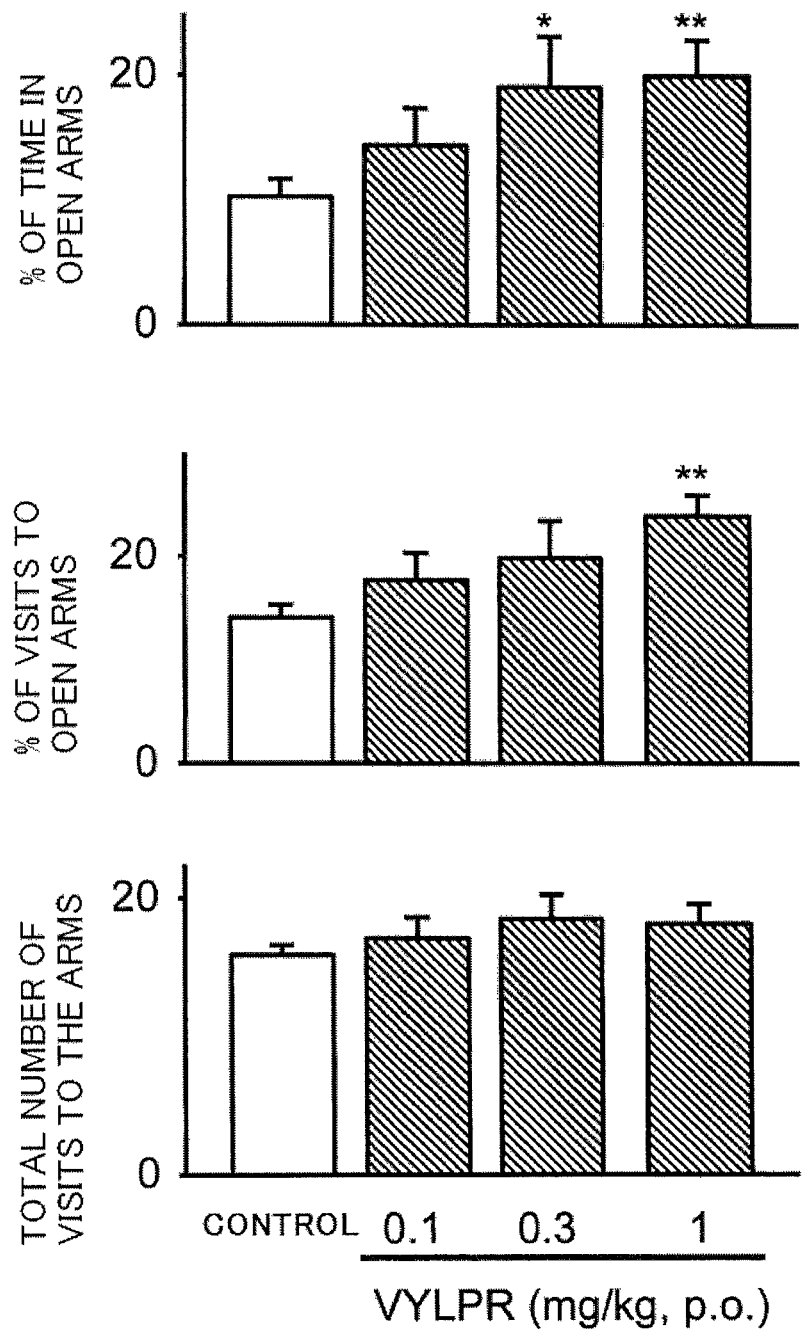
FIG. 3 shows the anxiolytic effect of orally administered VYLPR (SEQ ID NO:1) (Example 1), mean±SEM (n=11 to 20), *$p<0.05$, **$p<0.01$ vs. control.
Figure 4:
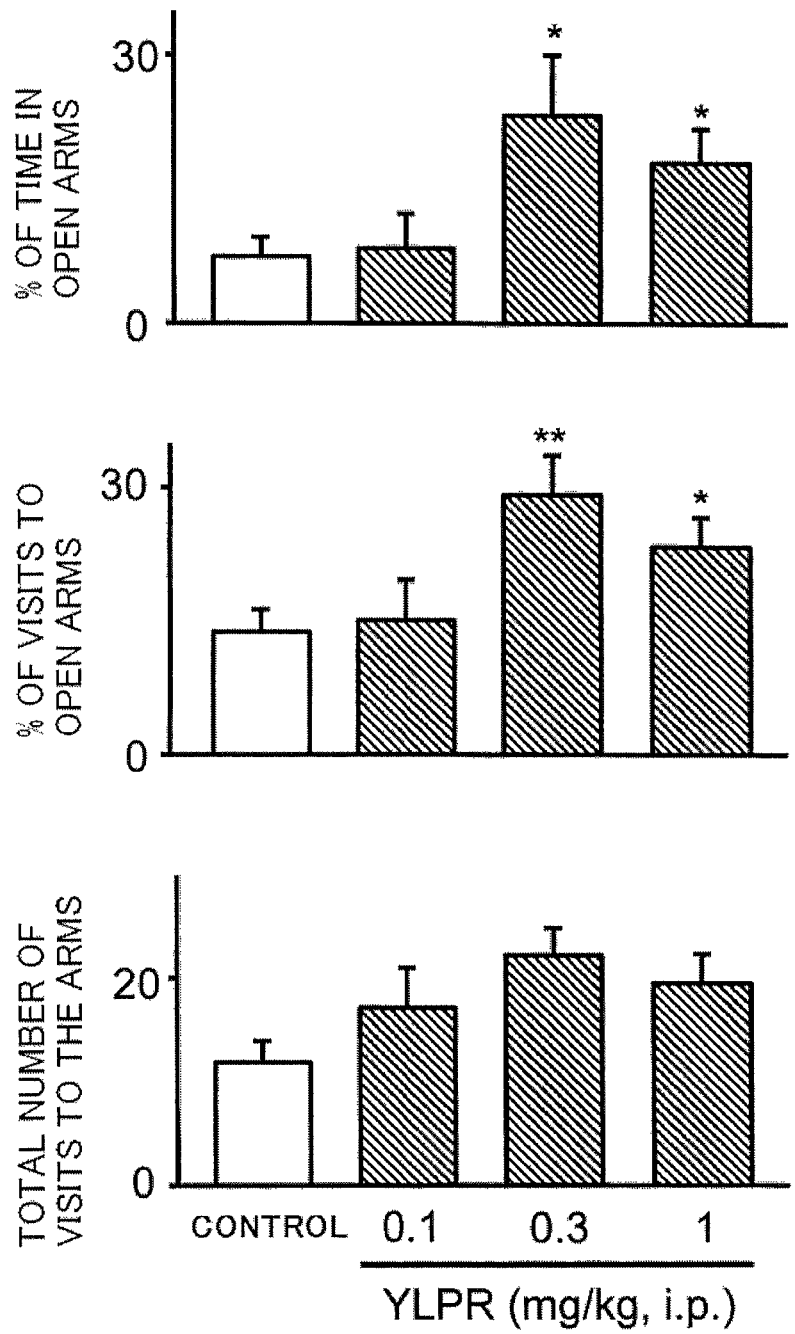
FIG. 4 shows the anxiolytic effect of intraperitoneally administered YLPR (SEQ ID NO:2) (Example 2), mean±SEM (n=5 to 11, *$p<0.05$, **$p<0.01$ vs. control.
Figure 5:
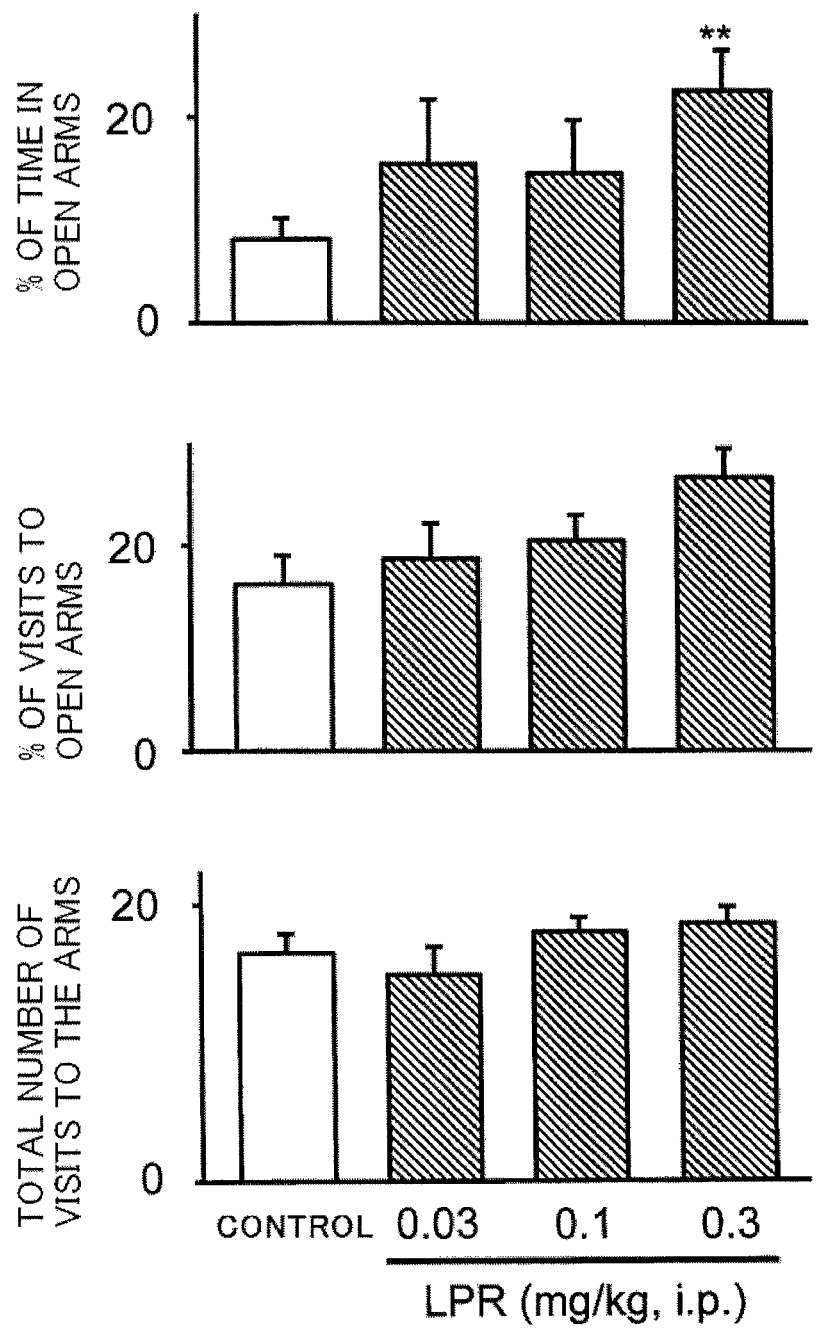
FIG. 5 shows the anxiolytic effect of intraperitoneally administered LPR (SEQ ID NO:3) (Example 3), mean±SEM (n=4 to 13, *$p<0.05$, **$p<0.01$ vs. control.
Figure 6:
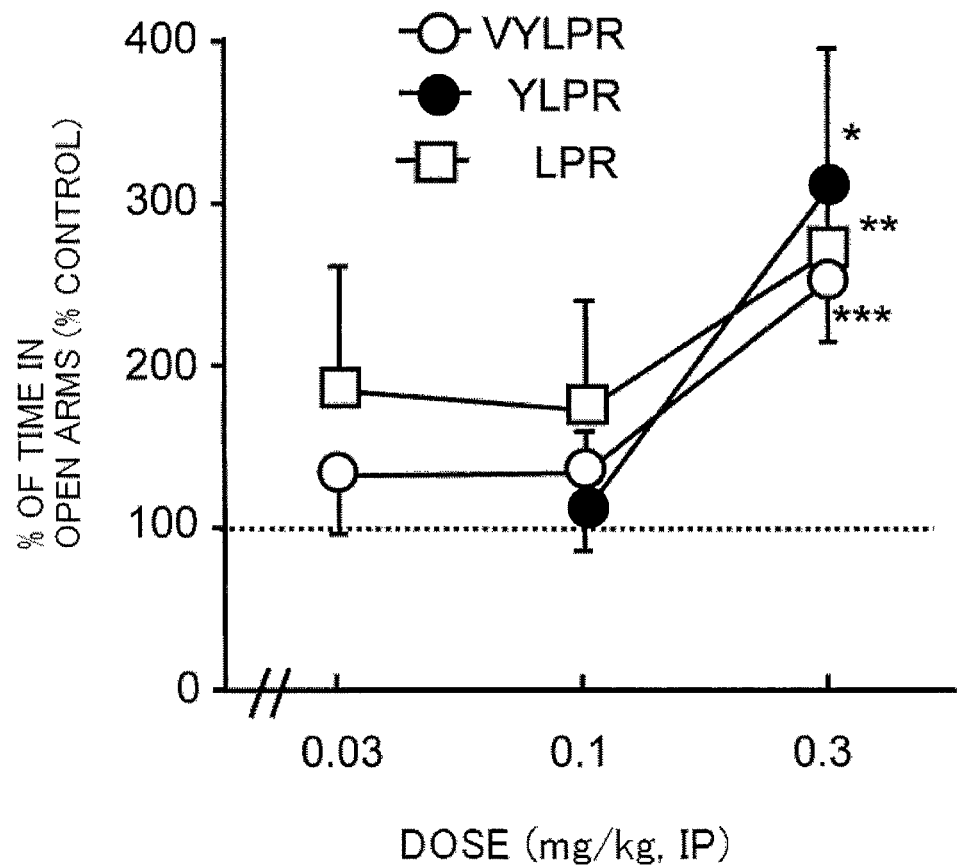
FIG. 6 shows the relationship between the structure and the activity regarding the anxiolytic effect of VYLPR (SEQ ID NO:1), mean±SEM (n=4 to 13, *$p<0.05$, $p<0.01$, *$p<0.001$.

In the present invention, the anxiolytic effects can be evaluated by the elevated plus-maze test, which has been developed as a method for evaluating anxiety-related behaviors to screen anxiolytic drugs and has been widely used (FIG. 1). Specifically, the test is performed as follows: a candidate substance for an anxiolytic drug is orally or intraperitoneally administered to a mouse, the mouse is placed in an elevated plus-maze 30 minutes after the administration, and the potency of the anxiolytic effect is evaluated based on the number of entries into the open arms and the change in the time spent on the open arms.

Because the anxiolytic effect of the peptide of the present invention was inhibited by indomethacin, which is an inhibitor of cyclooxygenase, the anxiolytic action is considered to be mediated by the release of prostaglandin (FIG. 7).

Because the anxiolytic effect of the peptide of the present invention was inhibited by BWA868C, i.e., a DP1 receptor ($DP_1$-R) antagonist, and SCH58261, i.e., an adenosine $A_{2A}$ receptor antagonist, the peptide is considered to promote the release of PGD2 and adenosine and thereby exhibit the anxiolytic effect (FIG. 10).

The anxiolytic effect of the peptide of the present invention was inhibited by the $GABA_A$ receptor antagonist bicuculline. This confirms that the effect of the peptide is mediated by a $GABA_A$ receptor (i.e., the peptide has an effect that is similar to that of $GABA_A$ receptor agonists or partial agonists) (FIG. 8). It is presumed that endogenous $GABA_A$ release is promoted. Given that the $GABA_A$ receptor is known to have a sleep-inducing effect, the peptides of the invention and analogs thereof are considered to have a sleep-inducing effect in addition to an anxiolytic effect and are also useful as sleep-inducing drugs.

The inventors previously found that soymorphin, a μ-opioid peptide derived from the primary soy protein β-conglycinin, shows an anxiolytic effect mediated by μ-opioid receptor (Patent Literature 1). The anxiolytic effect of the peptide of the invention was not inhibited by the μ-opioid receptor antagonist naloxone. This confirms that the anxiolytic effect of the peptides of the present invention is not mediated by a pt-opioid receptor, unlike the peptide disclosed in Patent Literature 1.

It is known that δ-opioid rubiscolin derived from Rubisco, a major protein from green leaves, demonstrates an anxiolytic effect by directly acting on the δ-opioid receptor and subsequently activating the $σ_1$ receptor. The anxiolytic effect of the peptide of the invention was not inhibited by the δ-opioid receptor antagonist naltrindole. This confirms that the anxiolytic effect of the peptides of the present invention is not mediated by a δ-opioid receptor.

Preferred active ingredients in the invention have been confirmed to be effective by oral administration.

Active Ingredients

The active ingredient of the anxiolytic drug of the invention is at least one peptide selected from the group consisting of Val-Tyr-Leu-Pro-Arg (SEQ ID NO:1), Tyr-Leu-Pro-Arg (SEQ ID NO:2), and Leu-Pro-Arg (SEQ ID NO:3). It was found that when incubation was performed at 37° C. for 5 hours after addition of trypsin to a heated ovalbumin solution, Val-Tyr-Leu-Pro-Arg (SEQ ID NO:1) was produced with a yield of about 44% on a molar basis. The active ingredient of the anxiolytic drug of the invention includes a hydrolysate obtained by hydrolyzing a protein comprising Val-Tyr-Leu-Pro-Arg (SEQ ID NO:1), such as ovalbumin, with a protease such as trypsin.

Each of the amino acids forming the peptide may be an L-amino acid, D-amino acid, or DL-amino acid (the mixture of D-amino acid and L-amino acid, including both a racemic amino acid and an amino acid containing an excess of either one of the two enantiomers). Preferably, the peptide contains only L-amino acids or only D-amino acids. Particularly, a peptide containing only L-amino acids is preferred.

Examples of salts of the peptide include acid addition salts and base salts. Examples of acid addition salts include salts with inorganic acids such as hydrochloric acid, sulfuric acid, nitric acid, phosphoric acid, hydrobromic acid, perchloric acid, and the like; and salts with organic acids such as citric acid, succinic acid, maleic acid, fumaric acid, malic acid, tartaric acid, p-toluenesulfonic acid, benzenesulfonic acid, methanesulfonic acid, trifluoroacetic acid, and the like. Examples of base salts include salts with alkali metals such as sodium, potassium, and lithium; and salts with alkaline earth metals such as calcium and magnesium.

Examples of solvates include solvates with water (hydrates), methanol, ethanol, isopropanol, acetic acid, tetrahydrofuran, acetone, dimethylformamide, dimethyl sulfoxide, dimethylacetamide, acetamide, ethylene glycol, propylene glycol, and dimethoxyethane.

Cases Where the Active Ingredient is a Peptide Analogue

The peptide analogs include the following analogs of the above-mentioned active ingredient peptides:
(1) N-terminal modified analogs;
(2) C-terminal modified analogs; and
(3) tyrosine residue analogs.

(1) The N-terminal amino group of the peptide may be an amino group monosubstituted or disubstituted with a straight or branched $C_1$-$C_4$ alkyl group, such as methylamino, dimethylamino, ethylamino, diethylamino, propylamino, dipropylamino, n-butylamino, di-n-butylamino, or the like. Alternatively, the N-terminal amino group or the side-chain amino group (when the peptide contains Lys) of the peptide may be monosubstituted or disubstituted with an aralkyl group such as benzyl, phenethyl, or the like; or modified with an acyl group, such as a straight or branched $C_1$-$C_6$ alkanoyl group, for example, formyl, acetyl, propionyl, butyryl, and isobutyryl, or a benzoyl group.

(2) The C-terminal carboxy group of the peptide may form an ester with a $C_1$-$C_6$ alkyl group such as methyl, ethyl, n-propyl, isopropyl, n-butyl, isobutyl, t-butyl, pentyl, hexyl, or the like; an ester with an aralkyl group such as benzyl, phenethyl, or the like; or an amide with an amine monosubstituted or disubstituted with a straight or branched $C_1$-$C_4$ alkyl group such as amino, methylamine, dimethylamine, ethylamine, diethylamine, propylamine, dipropylamine, n-butylamine, di-n-butylamine, or the like, or an amide with ammonia.

(3) Examples of a tyrosine residue analog (I) include residues represented by the following formula (I):

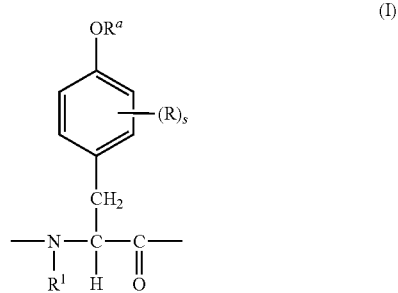

Wherein s is an integer from 0 to 4, and $R^1$ is a straight or branched $C_1$-$C_6$ alkyl group, aralkyl group, or hydrogen atom; $R^a$ is any of a protecting group cleavable in an acidic condition, such as a hydrogen atom, an alkali metal, an alkaline earth metal, methoxymethyl, 2-tetrahydrofuranyl, or 2-tetrahydropyranyl, methyl, or trifluoromethyl; R is each independently a straight or branched $C_1$-$C_6$ alkyl group (for example, methyl, ethyl, n-propyl, isopropyl, n-butyl, isobutyl, t-butyl, pentyl, or hexyl), an aralkyl group (for example, benzyl or hexyl), a straight or branched $C_1$-$C_6$ alkoxy group (for example, methoxy, ethoxy, n-propyloxy, isopropyloxy, n-butoxy, isobutoxy, t-butoxy, pentoxy, or hexyloxy), SH, a straight or branched $C_1$-$C_6$ alkylthio group (for example, methylthio, ethylthio, n-propylthio, isopropylthio, n-butylthio, isobutylthio, t-butylthio, pentylthio, or hexylthio), CN, $NO_2$, a halogen atom (F, Cl, Br, or I), amino ($NH_2$), a mono- or di-($C_1$-$C_6$ lower alkyl)amino (for example, methylamino, ethylamino, propylamino, butylamino, dimethylamino, diethylamino, dipropylamino, or dibutylamino), acetamide, acetyl, trifluoromethyl, or hydroxy; or two adjacent R or adjacent R and $OR^a$ are linked to form methylenedioxy or ethylenedioxy.

The peptide of the invention can be obtained by hydrolyzing a natural protein or polypeptide, or by chemical synthesis. An example of proteins and polypeptides to be hydrolyzed includes ovalbumin. The results of the Examples below confirmed that the tryptic digest of ovalbumin exhibits anxiolytic effects, whether it is administered intraperitoneally or orally (FIG. 11).

The hydrolysis of proteins may be performed using, for example, a hydrolase such as trypsin, chymotrypsin, papain, pepsin, carboxypeptidase, thermolysin, subtilisin, or the like derived from an animal, plant, or microorganism. The peptide of the invention used as an active ingredient can be obtained by using any of these enzymes, adjusting the pH to a suitable value to the enzyme, and allowing the reaction to proceed for about 30 minutes to about 48 hours at about 30 to about 40° C. The peptide of the invention may be purified from the resulting reaction mixture prior to use. When the peptide is obtained by enzymatic degradation of a food material, it may be used as it is, or incorporated into a different food material to prepare a food or food composition. The hydrolysis may be performed by reacting a protein in water for 30 minutes to 48 hours at 1 to 100° C. in the presence of a strong acid (for example, hydrochloric acid, nitric acid, or sulfuric acid) or a strong base (for example, an alkali metal hydroxide such as sodium hydroxide, potassium hydroxide, lithium hydroxide, or the like; an alkali metal carbonate such as sodium carbonate, potassium carbonate, or the like; or an alkali metal hydrogencarbonate such as sodium hydrogencarbonate, potassium hydrogencarbonate, or the like), to thereby produce the active ingredient peptide of the invention. The hydrolysis product may be used as it is after pH adjustment, or purified to separate the active ingredient peptide that is to be used.

The peptide of the invention can also be obtained by a peptide synthesis method. Specifically, the condensation can be performed by solution-phase or solid-phase methods generally used in peptide synthesis, such as a method in which a reactant having a reactive carboxy group and a reactant having a reactive amino group are reacted using an active ester such as HBTU, or a method using a coupling agent such as carbodiimide. When the resulting condensation product has a protecting group, the peptide can also be produced by removing the protecting group.

Functional groups that should not be involved in the reaction in this reaction step are protected with protecting groups. Examples of amino-protecting groups include benzyloxycarbonyl (CBZ), t-butyloxycarbonyl (Boc), 9-fluorenylmethyloxycarbonyl (Fmoc), and the like. Examples of carboxy-protecting groups include groups capable of forming alkyl esters, benzyl esters, and the like. In the case of a solid-phase method, the C-terminal carboxy group is bonded to a support such as chlorotrityl resin, chloromethyl resin, oxymethyl resin, p-alkoxybenzyl alcohol resin, or the like. The condensation reaction is carried out in the presence of a condensing agent such as carbodiimide, or using an N-protecting amino acid active ester or a peptide active ester.

The protecting group is removed after the completion of the condensation reaction. In the case of a solid-phase method, the bond between the C-terminus of the peptide and the resin is also cleaved. Furthermore, the peptide of the invention is purified according to a general method. Examples of purification methods include ion-exchange chromatography, reverse-phase liquid chromatography, affinity chromatography, and the like. The resulting peptide is analyzed by the Edman degradation technique, using a protein sequencer, GC-MS, or the like that reads an amino acid sequence from the C-terminus.

The peptide of the invention can also be synthesized according to an enzymatic method (see WO2003/010307, the content of which is incorporated herein by reference.)

The route of administration of the peptide of the invention is not particularly limited. The peptide can be administered orally, parenterally, or intrarectally. The peptide can be administered orally or non-orally. The dose of the peptide will vary depending on the type of compound, the mode of administration, and the age, condition, and the like of an individual who is administered the peptide; however, the daily dose for an adult is typically 0.01 to 500 mg/kg, preferably 0.05 to 100 mg/kg, and more preferably 0.1 to 30 mg/kg. The peptide (active ingredient) of the invention is typically administered in the form of a pharmaceutical composition in admixture with a pharmaceutical carrier. A pharmaceutical carrier that is commonly used in the field of pharmaceutical preparations and that does not react with the peptide of the invention is used.

The peptide of the invention can be used by itself as a foodstuff or a pharmaceutical, or can be made into a food preparation or a pharmaceutical preparation, either alone or together with suitable nontoxic carriers for oral administration, or with diluents or excipients. Examples of such food or pharmaceutical preparations include tablets (uncoated tablets, sugar-coated tablets, effervescent tablets, film-coated tablets, chewable tablets, and the like), capsules, troches, powders, fine granules, granules, solutions, suspensions, emulsions, pastes, creams, injections (including infusions such as amino acid infusions and electrolytes), and sustained-release preparations such as enteric-coated tablets, capsules, granules, and the like. The amount of the peptide in the food can be suitably selected but is typically in the range of from 0.01 to 100 wt %.

Specific examples of pharmaceutical carriers or carriers for oral administration, diluents, excipients, and like substances that can be added to a pharmaceutical or a food include lactose, glucose, mannite, dextrin, cyclodextrin, starch, saccharose, magnesium aluminometasilicate, synthetic aluminum silicate, sodium carboxymethyl cellulose, hydroxypropyl starch, calcium carboxymethyl cellulose, ion exchange resins, methylcellulose, gelatin, gum arabic, hydroxypropylcellulose, hydroxypropylmethylcellulose, polyvinylpyrrolidone, polyvinyl alcohol, light anhydrous silicic acid, magnesium stearate, talc, tragacanth, bentonite, veegum, titanium oxide, sorbitan fatty acid esters, sodium lauryl sulfate, glycerin, fatty acid glycerol esters, purified lanolin, glycerogelatin, polysorbate, macrogol, vegetable oils, waxes, liquid paraffin, white petrolatum, fluorocarbon, nonionic surfactants, propylene glycol, water, and the like.

Examples of dosage form include tablets, capsules, granules, powders, syrups, suspensions, suppositories, ointments, creams, gels, patches, inhalants, injections, and the like. These preparations are prepared according to general methods. Liquid preparations may be dissolved or suspended in water or other suitable solvents prior to use. Tablets and granules may be coated using known methods. Injections are prepared by dissolving the peptide of the invention in water. As required, injections may also be prepared by dissolving the peptide in physiological saline or a glucose solution, or may additionally contain a buffer or a preservative.

These preparations may contain the peptide of the invention in an amount of from 0.01 to 100 wt %, and preferably from 1 to 90 wt %. These preparations may also contain another therapeutically beneficial ingredient(s).

Solid preparations for oral administration may be prepared by mixing an active ingredient with an excipient such as lactose, starch, crystalline cellulose, calcium lactate, silicic acid anhydride, and the like to form powders. Further, a binder such as saccharose, hydroxypropylcellulose, and polyvinylpyrrolidone; and a disintegrator such as carboxymethyl cellulose and calcium carboxymethyl cellulose may be also added and the resulting mixture is dry- or wet-granulated to form granules. Tablets may be prepared by tableting these powders or granules as they are, or after adding thereto lubricants such as magnesium stearate and talc. These granules or powders can be coated with enteric coatings such as hydroxypropylmethylcellulose phthalate and methacrylate-methyl methacrylate polymer to form enteric-coated preparations; or coated with ethylcellulose, carnauba wax, or hydrogenated oil to form sustained-release preparations. Capsules may be prepared by filling hard gelatin capsules with the powders or granules, or by coating with gelatin films the active ingredient as it is, or after being dissolved in glycerin, polyethylene glycol, sesame oil, olive oil, or the like to form soft gelatin capsules.

Liquid preparations for oral administration may be prepared by dissolving in water the active ingredient together with sweetening agents such as saccharose, sorbitol, and glycerin to form transparent syrups; by further adding thereto essential oils, ethanol, and the like to form elixirs; or by further adding thereto gum arabic, tragacanth, polysorbate 80, sodium carboxymethyl cellulose, or the like to form emulsions or suspensions. These liquid preparations may optionally contain taste-improving agents, coloring agents, preservatives, or the like.

Injections may be prepared by dissolving the active ingredient in distilled water for injection, optionally with a pH adjuster such as hydrochloric acid, sodium hydroxide, lactose, lactic acid, sodium, sodium monohydrogen phosphate, and sodium dihydrogen phosphate, and an isotonic agent such as sodium chloride and glucose, and filling an ampoule with the solution after the sterile filtration; or by further adding thereto mannitol, dextrin, cyclodextrin, gelatin, or the like, followed by vacuum freeze-drying, to form injections that are reconstituted prior to use. Emulsions for injection can also be prepared by adding to the active ingredient lecithin, polysorbate 80, polyoxyethylene hydrogenated castor oil, or the like, and emulsifying the mixtures in water.

Preparations for rectal or vaginal administration may be prepared by humidifying and dissolving the active ingredient together with a suppository bases such as cacao butter, tri-, di-, and monoglycerides of fatty acids, or polyethylene glycol, and by pouring the mixture into a mold, followed by cooling; or by dissolving the active ingredient in polyethylene glycol, soybean oil, or the like, followed by coating the mixture with a gelatin film.

External preparations for the skin may be prepared by adding the active ingredient to white petrolatum, yellow beeswax, liquid paraffin, polyethylene glycol, and the like, and by optionally humidifying and kneading the mixtures to form an ointment; or by kneading the active ingredient with an adhesive such as rosin and acrylic acid alkyl ester polymers, followed by spreading the mixture onto a nonwoven cloth such as polyalkyl to form a tape.

Specific examples of forms of foods that can be prepared by adding or blending the peptides of the invention include beverages (for example, coffee, cocoa, juices, soft drinks, mineral drinks, tea beverages, green tea, black tea, oolong tea, milk beverages, lactic acid bacteria beverages, yoghurt beverages, and carbonated beverages), gum, gummy candies, jellies, candies, cookies, crackers, biscuits, ice confectioneries (for example, ice creams, ice candies, sherbets, and shaved ice), retort-pouched foods, jelly-like foods (for example, jellies, agar jelly, and jelly-like beverages), and the like. Foods that can be prepared by adding or blending the peptides of the invention may take the form of health foods, functional foods, nutritional supplements, dietary supplements, foods for specified health uses, foods for the ill/combined foods for the ill (a category of foods for special dietary uses, approved by the Ministry of Health, Labour and Welfare, Japan), and foods for the elderly (a category of foods for special dietary uses, approved by the Ministry of Health, Labour and Welfare, Japan). These foods may be in the form of uncoated tablets, film-coated tablets, sugar-coated tablets, granules, powders, tablets, capsules (including both hard and soft gelatin capsules), chewable forms, syrups, drinks, and the like. The preparation of foods obtained by adding or blending the peptides of the invention can be performed according to known methods.

EXAMPLES

The present invention will be described in greater detail below with reference to the Examples. The following Examples, however, do not limit the scope of the invention.

Elevated Plus-Maze Experiment

The elevated plus-maze includes two open arms (25×5 cm) and two closed arms (25×5×15 cm), which were joined to a central platform 50 cm high above the floor (see FIG. 1). Because the closed arms were surrounded by barriers, a mouse could safely walk in the closed arms in spite of the elevated position. On the other hand, because the open arms were not surrounded by barriers, a mouse walking along the open arms would feel anxious that it might fall from the elevated position. Therefore, the more time the mouse spent in the open arms, or the greater the number of entries into the open arms, the less anxious the mouse would feel. Thus, the anxiolytic activity is determined based on these indices.

A mouse was placed on a portion of the central platform facing one of the open arms, and the test was started. During the 5-minute test time, the cumulative time spent in the open arms (abbr.: time in open arms), the number of visits to the open arms (abbr.: visits to open arms), and the total number of visits to the either arms (abbr.: total visits) were recorded. The percentage of the time spent in the open arms and the percentage of the number of visits to the open arms were calculated as indices of anxiety.

Statistical Analysis

The data obtained from the elevated plus-maze test were represented as the mean values±SEM. The data were analyzed by one-way ANOVA, followed by the Fisher test for multiple comparisons.

Examples 1 to 3

Anxiolytic Effects

Experiments and Results

Each of VYLPR (SEQ ID NO:1) (Example 1), YLPR (SEQ ID NO:2) (Example 2), and LPR (SEQ ID NO:3) (Example 3) dissolved in physiological saline was administered intraperitoneally (IP) or orally (PO) to mice (n=3 to 14) in the amount shown in each figure before the mice were placed on the central portion of the elevated plus-maze. The percentage of the time spent in the open arms, the percentage of the number of visits to the open arms, and the total number of visits to the both arms (total visits) were compared between groups administered each peptide and the control group (0 mg/kg). The results are shown in FIGS. 2 to 5, FIGS. 7 and 8, and Table 1. As shown in FIGS. 2 to 5, FIGS. 7 and 8, and Table 1, the peptides of the invention significantly increased or showed a significant tendency to increase the percentage of visits to the open arms and the percentage of the time spent in the open arms.

TABLE 1

Relationship between the Structure and the activity regarding the Anxiolytic Effect of each Low-molecular-weight Peptide

| Peptide Administered | Minimum Effective Dose (mg/kg, IP) |
|---|---|
| VYLPR | 0.3 |
| YLPR | 0.3 |
| LPR | 0.3 |

Example 4

Trypsin-digested ovalbumin was used as an active ingredient and was administered intraperitoneally and orally to test the anxiolytic effects using the open arms in the same manner as in Examples 1 to 3. The results are shown in FIG. 11.

An aqueous solution of ovalbumin (20 mg/ml) was heated (10-min boiling), and bovine trypsin (E:S=1:100) was added to carry out a reaction at 37° C. for 5 hours. As a result, VYLPR (SEQ ID NO:1) was produced at a high efficiency of 44 mol %. When the aqueous solution of ovalbumin was not pre-heated, VYLPR (SEQ ID NO:1) was below the detection limit and was hardly produced even with the trypsin treatment. TPCK-treated Trypsin from bovine pancreas (Sigma) was used as the bovine trypsin.

Considering the possibility that the anxiolytic effects might arise from the administration of an undigested product since trypsin is present in the digestive tract, a group administered an undigested product (with and without heat treatment) was used as the control.

Test Example 1

An anxiolytic peptide of the invention was administered in combination with the inhibitor or one of the antagonists for various receptors as follows, and tests were conducted in the same manner as in Example 1 in order to identify the effect of each antagonist on the anxiolytic activity of the peptide of the present invention, i.e., to identify the receptors on which the peptide of the invention acts.
COX inhibitor: Indomethacin, 10 mg/kg
$DP_1$-R antagonist: BWA868C, 60 µg/kg
A2A-R antagonist: SCH58261, 0.1 mg/kg The results are shown in FIGS. 7, 8, and 10.

From these results, the peptide of the present invention is presumed to have the action pathway shown in FIG. 9.

INDUSTRIAL APPLICABILITY

The anxiolytic peptide of the invention potentially has an action mechanism that is different from those of the conventional anxiolytic drugs, and thus can provide novel types of pharmaceuticals and foods.

The invention claimed is:

1. An isolated peptide selected from the group consisting of:
an amino-terminal modified peptide of SEQ ID NO:1 or SEQ ID NO:2 or SEQ ID NO:3, wherein the amino-terminal modification comprises an amino group mono-substituted or disubstituted with a straight or branched $C_1$-$C_4$ alkyl group, an aralkyl group, an acyl group, a straight or branched $C_1$-$C_6$ alkanoyl group,
a carboxy-terminal modified peptide of SEQ ID NO:1 or SEQ ID NO:2 or SEQ ID NO:3, wherein the carboxy-terminal modification comprises an ester with a $C_1$-$C_6$ alkyl group, an ester with an aralkyl group, an amide with an amine monosubstituted or disubstituted with a straight or branched $C_1$-$C_4$ alkyl group, or an amide with ammonia, and,
a tyrosine residue modified peptide of SEQ ID NO:1 or SEQ ID NO:2, wherein the tryosine modification comprises a modification having the chemical formula:

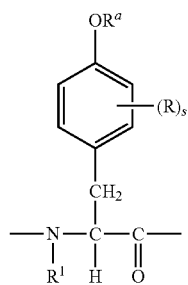

(I)

wherein:
$R^1$ is a straight or branched $C_1$-$C_6$ alkyl group, aralkyl group, or hydrogen atom;
$R^a$ is a protecting group cleavable in an acidic condition, an alkali metal, an alkaline earth metal, methoxymethyl, 2-tetrahydrofuranyl, 2-tetrahydropyranyl, methyl, or trifluoromethyl;
R is each independently a straight or branched $C_1$-$C_6$ alkyl group, an aralkyl group, a straight or branched $C_1$-$C_6$ alkoxy group, SH, a straight or branched $C_1$-$C_6$ alkylthio group, CN, $NO_2$, a halogen, $NH_2$, a mono- or di-($C_1$-$C_6$ lower alkyl)amino, acetamide, acetyl, trifluoromethyl, hydroxy;
or two adjacent R or adjacent R and $OR^a$ are linked to form methylenedioxy or ethylenedioxy, and
s is an integer from 0 to 2.

2. A pharmaceutical composition comprising
a) a peptide selected from the group consisting of:
an amino-terminal modified peptide of SEQ ID NO:1 or SEQ ID NO:2 or SEQ ID NO:3, wherein the amino-terminal modification comprises an amino group mono-substituted or disubstituted with a straight or branched $C_1$-$C_4$ alkyl group, an aralkyl group, an acyl group, a straight or branched $C_1$-$C_6$ alkanoyl group,
a carboxy-terminal modified peptide of SEQ ID NO:1 or SEQ ID NO:2 or SEQ ID NO:3, wherein the carboxy-terminal modification comprises an ester with a $C_1$-$C_6$ alkyl group, an ester with an aralkyl group, an amide with an amine monosubstituted or disubstituted with a straight or branched $C_1$-$C_4$ alkyl group, or an amide with ammonia, and,
a tyrosine residue modified peptide of SEQ ID NO:1 or SEQ ID NO:2, wherein the tryosine modification comprises a modification having the chemical formula:

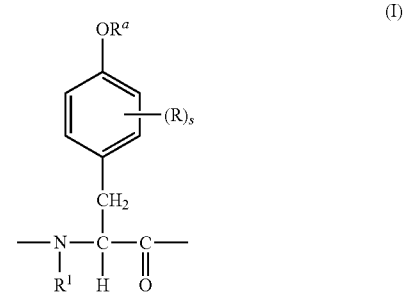

(I)

wherein:
$R^1$ is a straight or branched $C_1$-$C_6$ alkyl group, aralkyl group, or hydrogen atom;
$R^a$ is a protecting group cleavable in an acidic condition, an alkali metal, an alkaline earth metal, methoxymethyl, 2-tetrahydrofuranyl, 2-tetrahydropyranyl, methyl, or trifluoromethyl;
R is each independently a straight or branched $C_1$-$C_6$ alkyl group, an aralkyl group, a straight or branched $C_1$-$C_6$ alkoxy group, SH, a straight or branched $C_1$-$C_6$ alkylthio group, CN, $NO_2$, a halogen, $NH_2$, a mono- or di-($C_1$-$C_6$ lower alkyl)amino, acetamide, acetyl, trifluoromethyl, hydroxy;
or two adjacent R or adjacent R and $OR^a$ are linked to form methylenedioxy or ethylenedioxy,
s is an integer from 0 to 2; and,
b) a pharmaceutical carrier;
wherein the pharmaceutical composition is an anxiolytic drug, a sleep-inducing drug, a sleep-enhancing drug, or an antidepressant drug.

3. An anxiolytic or sleep-enhancing food comprising a peptide selected from the group consisting of:
- an amino-terminal modified peptide of SEQ ID NO:1 or SEQ ID NO:2 or SEQ ID NO:3, wherein the amino-terminal modification comprises an amino group mono-substituted or disubstituted with a straight or branched $C_1$-$C_4$ alkyl group, an aralkyl group, an acyl group, a straight or branched $C_1$-$C_6$ alkanoyl group,
- a carboxy-terminal modified peptide of SEQ ID NO:1 or SEQ ID NO:2 or SEQ ID NO:3, wherein the carboxy-terminal modification comprises an ester with a $C_1$-$C_6$ alkyl group, an ester with an aralkyl group, an amide with an amine monosubstituted or disubstituted with a straight or branched $C_1$-$C_4$ alkyl group, or an amide with ammonia, and,
- a tyrosine residue modified peptide of SEQ ID NO:1 or SEQ ID NO:2, wherein the tryosine modification comprises a modification having the chemical formula:

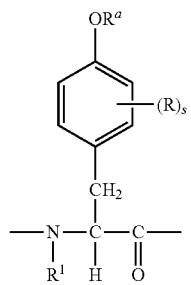

(I)

wherein:
$R^1$ is a straight or branched $C_1$-$C_6$ alkyl group, aralkyl group, or hydrogen atom;
$R^a$ is a protecting group cleavable in an acidic condition, an alkali metal, an alkaline earth metal, methoxymethyl, 2-tetrahydrofuranyl, 2-tetrahydropyranyl, methyl, or trifluoromethyl;
R is each independently a straight or branched $C_1$-$C_6$ alkyl group, an aralkyl group, a straight or branched $C_1$-$C_6$ alkoxy group, SH, a straight or branched $C_1$-$C_6$ alkylthio group, CN, $NO_2$, a halogen, $NH_2$, a mono- or di-($C_1$-$C_6$ lower alkyl)amino, acetamide, acetyl, trifluoromethyl, hydroxy;
or two adjacent R or adjacent R and $OR^a$ are linked to form methylenedioxy or ethylenedioxy, and
s is an integer from 0 to 2.

4. A method for relieving anxiety or enhancing sleep, comprising orally administering to a subject in need thereof an effective amount of at least one peptide selected from the group consisting of:
- a peptide consisting of the amino acid sequence Val-Tyr-Leu-Pro-Arg (SEQ ID NO: 1),
- a peptide consisting of the amino acid sequence Tyr-Leu-Pro-Arg (SEQ ID NO:2),
- a peptide consisting of the amino acid sequence Leu-Pro-Arg (SEQ ID NO:3),
- an amino-terminal modified peptide of SEQ ID NO:1 or SEQ ID NO:2 or SEQ ID NO:3, wherein the amino-terminal modification comprises an amino group mono-substituted or disubstituted with a straight or branched $C_1$-$C_4$ alkyl group, an aralkyl group, an acyl group, a straight or branched $C_1$-$C_6$ alkanoyl group,
- a carboxy-terminal modified peptide of SEQ ID NO:1 or SEQ ID NO:2 or SEQ ID NO:3, wherein the carboxy-terminal modification comprises an ester with a $C_1$-$C_6$ alkyl group, an ester with an aralkyl group, an amide with an amine monosubstituted or disubstituted with a straight or branched $C_1$-$C_4$ alkyl group, or an amide with ammonia, and,
- a tyrosine residue modified peptide of SEQ ID NO:1 or SEQ ID NO:2, wherein the tryosine modification comprises a modification having the chemical formula:

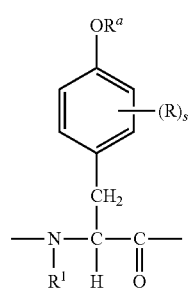

(I)

wherein:
$R^1$ is a straight or branched $C_1$-$C_6$ alkyl group, aralkyl group, or hydrogen atom;
$R^a$ is a protecting group cleavable in an acidic condition, an alkali metal, an alkaline earth metal, methoxymethyl, 2-tetrahydrofuranyl, 2-tetrahydropyranyl, methyl, or trifluoromethyl;
R is each independently a straight or branched $C_1$-$C_6$ alkyl group, an aralkyl group, a straight or branched $C_1$-$C_6$ alkoxy group, SH, a straight or branched $C_1$-$C_6$ alkylthio group, CN, $NO_2$, a halogen, $NH_2$, a mono- or di-($C_1$-$C_6$ lower alkyl)amino, acetamide, acetyl, trifluoromethyl, hydroxy;
or two adjacent R or adjacent R and $OR^a$ are linked to form methylenedioxy or ethylenedioxy, and
s is an integer from 0 to 2, wherein the effective amount is a dose of between 0.005 to 100 mg/kg.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial
<220> FEATURE:
<223> OTHER INFORMATION: Designed peptide

<400> SEQUENCE: 1

Val Tyr Leu Pro Arg
```

```
<210> SEQ ID NO 2
<211> LENGTH: 4
<212> TYPE: PRT
<213> ORGANISM: Artificial
<220> FEATURE:
<223> OTHER INFORMATION: Designed peptide

<400> SEQUENCE: 2

Tyr Leu Pro Arg
 1
```